United States Patent
Thompson et al.

(10) Patent No.: US 6,476,041 B1
(45) Date of Patent: Nov. 5, 2002

(54) 1,4 SUBSTITUTED PIPERIDINYL NMDA/NR2B ANTAGONISTS

(75) Inventors: Wayne Thompson, Lansdale; David A. Claremon, Maple Glen; Peter M. Munson, Harleysville, all of PA (US); Janusz Kulagowski, Sawbridgeworth (GB); Willie Whitter, West Point, PA (US); Ian Huscroft, Bishops Stortford (GB)

(73) Assignee: Merck & Co., Inc., Rahway, NJ (US)

( * ) Notice: Subject to any disclaimer, the term of this patent is extended or adjusted under 35 U.S.C. 154(b) by 0 days.

(21) Appl. No.: 09/696,504

(22) Filed: Oct. 25, 2000

Related U.S. Application Data
(60) Provisional application No. 60/162,352, filed on Oct. 29, 1999.

(51) Int. Cl.[7] .................... C07D 473/00; C07D 277/04; C07D 471/02; A61K 31/445
(52) U.S. Cl. .................. 514/263.22; 546/199; 546/201; 546/118; 514/322; 514/323; 514/309; 544/264
(58) Field of Search ................. 546/199, 201, 546/118; 514/322, 323, 259, 303, 263.22; 544/283, 264

(56) References Cited

U.S. PATENT DOCUMENTS

| | | | | |
|---|---|---|---|---|
| 4,493,837 A | * | 1/1985 | Sugimoto et al. | 424/253 |
| 5,306,723 A | | 4/1994 | Chenard | 514/304 |
| 5,436,255 A | | 7/1995 | Butler | 514/320 |

FOREIGN PATENT DOCUMENTS

| | | | |
|---|---|---|---|
| EP | 441506 | | 8/1991 |
| EP | 787493 | | 8/1997 |
| EP | 0846683 | * | 12/1997 |
| EP | 846683 | | 6/1998 |
| WO | WO 91/17156 | | 11/1991 |
| WO | WO 92/18502 | | 10/1992 |
| WO | WO 93/02052 | | 2/1993 |
| WO | WO 94/21615 | * | 9/1994 |
| WO | WO 94/24105 | * | 10/1994 |
| WO | WO 96/02250 | | 2/1996 |
| WO | WO 96/37226 | | 11/1996 |
| WO | WO 98/18793 | | 5/1998 |
| WO | WO 00/00197 | | 1/2000 |

OTHER PUBLICATIONS

CAS printout for NOda et al.*
Lipton et al. Exitatory anino acids as a final common pathway for neurologic disorders, New England J. of Med., 1994 330: 613–622.*
J.D. Kristensen et al., Pain, 51:249–253(1992).
P.K. Eide et al., Pain, 61:221–228(1995).
D.J. Knox et al., Anaesth. Intensive Care, 23:620–622(1995).
M.B. Max et al., Clin. Neuropharmacol., 18:360–368(1995).
T. Ishii et al., J. Biol. Chem., 268:2836–2843(1993).
D.J. Laurie et al., Mol. Brain Res., 51:23–32(1997).
S. Boyce et al., Neuropharmacology, 28:611–623(1999).
Z.-L. Zhou et al., J. Med. Chem., 42:2993–3000(1999).
Electronic Database Printout 1999:617466 Caplus, T.F. Gregory et al., Poster #94, 218th Nat. Meeting ACS, N. Orleans, Aug. 22–26, 1999.
J.N.C. Kew et al., Brit. J. Pharmacol., 123:463–472(1998).
M. Lai et al., Int. J. Clin. Pharmacol. Res., 17:101–103(1997).

* cited by examiner

Primary Examiner—Mukund J. Shah
Assistant Examiner—Hong Liu
(74) Attorney, Agent, or Firm—Shu M. Lee; David L. Rose

(57) ABSTRACT

Novel piperidinyl compounds substituted in the 1- and 4-positions are effective as NMDA NR2B antagonists useful for relieving pain.

9 Claims, No Drawings

1,4 SUBSTITUTED PIPERIDINYL NMDA/NR2B ANTAGONISTS

This application claims the benefit of U.S. Provisional Application No. 60/162,352, filed on Oct. 29, 1999.

BACKGROUND OF THE INVENTION

Field of the Invention

This invention relates to novel 1,4 substituted piperidines. In particular, this invention relates to piperidines substituted in the 1- and 4-positions, through a bridge, with i) optionally substituted 2-benzimidazoles, 2-indoles, 2-quinazolines, or 2-imidazopyridines; or ii) phenyl or substituted phenyl that are effective as NOVA NR2B antagonists useful for relieving pain.

Ions such as glutamate play a key role in processes related to chronic pain and pain-associated neurotoxicity—primarily by acting through N-methyl-D-aspartate ("NMDA") receptors. Thus, inhibition of such action—by employing ion channel antagonists, particularly NMDA antagonists—can be beneficial in the treatment and control of pain.

Known NMDA antagonists include ketamine, dextromophan, and 3-(2-carboxypiperazin-4-yl)-propyl-1-phosphonic acid ("CPP"). Although these compounds have been reported (J. D. Kristensen, et al., *Pain*, 51:249–253 (1992); K. Eide, et al., *Pain*, 61:221–228 (1995); D. J. Knox, et al., *Anaesth. Intensive Care* 23:620–622 (1995); and M. B. Max, et al., *Clin. Neuropharmacol.* 18:360–368 (1995)) to produce symptomatic relief in a number of neuropathies including postherpetic neuralgia, central pain from spinal cord injury, and phantom limb pain, widespread use of these compounds is precluded by their undesirable side effects. Such side effects at analgesic doses include psychotomimetic effects such as dizziness, headache, hallucinations, dysphoria, and disturbances of cognitive and motor function. Additionally, more severe hallucinations, sedation, and ataxia are produced at doses only marginally higher than analgesic doses. Thus, it would be desirable to provide novel NMDA antagonists that are absent of undesirable side effects or that produce fewer and/or milder side effects.

NMDA receptors are heteromeric assemblies of subunits, of which two major subunit families designated NR1 and NR2 have been cloned. Without being bound by theory, it is generally believed that the various functional NMDA receptors in the mammalian central nervous system ("CNS") are only formed by combinations of NR1 and NR2 subunits, which respectively express glycine and glutamate recognition sites. The NR2 subunit family is in turn divided into four individual subunit types: NR2A, NR2B, NR2C, and NR2D. I. Ishii, et al., *J. Biol. Chem.*, 268:2836–2843 (1993), A. Wenel, et al., *Neural Report*, 7:45–48 (1995), and D. J. Laurie et al., *Mol. Brain Res.*, 51:23–32 (1997) describe how the various resulting combinations produce a variety of NMDA receptors differing in physiological and pharmacological properties such as ion gating properties, magnesium sensitivity, pharmacological profile, as well as in anatomical distribution.

For example, while NR1 is found throughout the brain, NR2 subunits are differentially distributed. In particular, it is believed that the distribution map for NR2B lowers the probability of side effects while producing pain relief. For example, S. Boyce, et al., *Neuropharmacology*, 38:611–623 (1999) describes the effect of selective NMDA NR2B antagonists on pain with reduced side-effects. Thus, it would be desirable to provide novel NMDA antagonists that target the NR2B receptor.

Phenol compounds described as NMDA antagonists are described in U.S. Pat. Nos. 5,306,723 and 5,436,255, and in International Patent Publications WO91/17156, WO92/19502, WO93/02052, WO94/29571, WO95/28057, WO96/37226, and EP 04422506. Benzyl piperidine substituted with phenols or imidazoles are described in Z.-L. Zhou, et al., *J. Medicinal Chemistry*, 42:2993–3000(1999); T. F. Gregory, et al., Poster #94, 218th National Meeting American Chemical Society, New Orleans, La., Aug. 22–26, 1999. Other NMDA NR2B selective compounds are described in European Patent Publication EP 787493 and British *J. Pharmacol.*, 123:463(1998). However, there continues to be a need for novel NMDA antagonists that target the NR2B receptor.

International Patent Publication WO94/21615 describes benzimidazole-piperidine compounds utilized as dopamine D4 antagonists.

SUMMARY OF THE INVENTION

The present invention relates to novel piperidines substituted in the 1- and 4-positions, through a bridge, with i) optionally substituted 2-benzimidazoles, 2-indoles, 2-quinazolines, or 2-imidazopyridines; or ii) phenyl or substituted phenyl. The present invention also forms pharmaceutical compositions utilizing the compounds. Further, this invention includes novel methods to treat pain by utilizing the compounds.

DETAILED DESCRIPTION OF THE INVENTION

In one aspect, the compounds of this invention are represented by Formula (I):

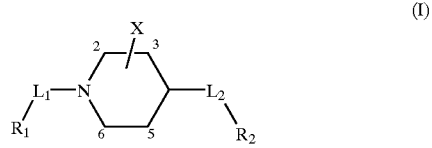

or pharmaceutically acceptable salts thereof, wherein $R_1$ is i) 2-benzimidazole, 2-imidazopyridine, 2-indole, purine, or 2-quinazoline, each optionally substituted with one to five substituents, each substituent independently being chloro, fluoro, bromo, $C_1$–$C_4$alkyl, trifluoromethyl, $C_1$–$C_4$alkylsulfonamide, hydroxy, or carboxy; or ii) phenyl, optionally substituted with one to five substituents, each substituent independently being chloro, fluoro, bromo, $C_1$–$C_4$alkyl, trifluoromethyl, $C_1$–$C_4$alkylsulfonamide, hydroxy, or carboxy;

$R_2$ is a) 2-benzimidazole, 2-imidazopyridine, 2-indole, purine, or 2-quinazoline, each optionally substituted with one to five substituents, each substituent independently being chloro, fluoro, bromo, $C_1$–$C_4$alkyl, trifluoromethyl, $C_1$–$C_4$alkylsulfonamide, hydroxy, or carboxy; or b) phenyl, optionally substituted with one to five substituents, each substituent independently being chloro, fluoro, bromo, $C_1$–$C_4$alkyl, trifluoromethyl, $C_1$–$C_4$alkylsulfonamide, hydroxy, or carboxy;

When $R_1$ is i, then $R_2$ is b; when $R_1$ is ii, then $R_2$ is a;

When $R_1$ or $R_2$ is 2-benzimidazole, respective $L_1$ or L2 is not $C_1$–$C_2$alkyl, except when $R_1$ or $R_2$ is hydroxy-substituted 2-benzimidazole, respective $L_1$ or $L_2$ includes $C_1$–$C_2$alkyl $L_1$ and $L_2$ are independently $C_1$–$C_4$alkyl, $C_1$–$C_4$alkenyl, $C_1$–$C_4$alkynyl, $C_1$–$C_4$alkoxy, amino$C_1$–$C_4$alkyl, hydroxy$C_1$–$C_4$alkyl, carbonyl, cyclo$C_3$–$C_6$alkyl or aminocarbonyl; and optionally substituted at any of the 2, 3, 5, or 6 positions independently with X, wherein X is hydroxy, amino, $C_1$–$C_4$alkylamino, di($C_1$–$C_4$)alkylamino, $C_1$–$C_4$alkyl, ester, carbamate, carbonate, or ether.

In an embodiment of this invention the compound is represented by Formula (I) or a pharmaceutically acceptable salt thereof, wherein $R_1$ is 2-imidazopyridine, optionally substituted with one to five substituents, each substituent independently being chloro, fluoro, bromo, $C_1$–$C_4$alkyl, trifluoromethyl, $C_1$–$C_4$alkylsulfonamide, hydroxy, or carboxy;

$R_2$ is phenyl, optionally substituted with one to five substituents, each substituent independently being chloro, fluoro, bromo, $C_1$–$C_4$alkyl, trifluoromethyl, $C_1$–$C_4$alkylsulfonamide, hydroxy, or carboxy;

$L_1$ and $L_2$ are independently $C_1$–$C_4$alkyl, $C_1$–$C_4$alkenyl, $C_1$–$C_4$alkynyl, $C_1$–$C_4$alkoxy, amino$C_1$–$C_4$alkyl, hydroxy$C_1$–$C_4$alkyl, carbonyl, cyclo$C_3$–$C_6$alkyl or aminocarbonyl; and optionally substituted at any of the 2, 3, 5, or 6 positions independently with X, wherein X is hydroxy, amino, $C_1$–$C_4$alkylamino, di($C_1$–$C_4$)alkylamino, $C_1$–$C_4$alkyl, ester, carbamate, carbonate, or ether.

In another embodiment of this invention the compound is represented by Formula (I) or a pharmaceutically acceptable salt thereof, wherein $R_1$ is purine, optionally substituted with one to five substituents, each substituent independently being chloro, fluoro, bromo, $C_1$–$C_4$alkyl, trifluoromethyl, $C_1$–$C_4$alkylsulfonamide, hydroxy, or carboxy;

$R_2$ is phenyl, optionally substituted with one to five substituents, each substituent independently being chloro, fluoro, bromo, $C_1$–$C_4$alkyl, trifluoromethyl, $C_1$–$C_4$alkylsulfonamide, hydroxy, or carboxy;

$L_1$ and $L_2$ are independently $C_1$–$C_4$alkyl, $C_1$–$C_4$alkenyl, $C_1$–$C_4$alkynyl, $C_1$–$C_4$alkoxy, amino$C_1$–$C_4$alkyl, hydroxy$C_1$–$C_4$alkyl, carbonyl, cyclo$C_3$–$C_6$alkyl or aminocarbonyl; and optionally substituted at any of the 2, 3, 5, or 6 positions independently with X, wherein X is hydroxy, amino, $C_1$–$C_4$alkylamino, di($C_1$–$C_4$)alkylamino, $C_1$–$C_4$alkyl, ester, carbamate, carbonate, or ether.

In still another embodiment of this invention the compound is represented by Formula (I) or a pharmaceutically acceptable salt thereof, wherein $R_1$ is 2-benzimidazole, optionally substituted with one to five substituents, each-substituent independently being chloro, fluoro, bromo, $C_1$–$C_4$alkyl, trifluoromethyl, $C_1$–$C_4$alkylsulfonamide, hydroxy, or carboxy;

$R_2$ is phenyl, optionally substituted with one to five substituents, each substituent independently being chloro, fluoro, bromo, $C_1$–$C_4$alkyl, trifluoromethyl, $C_1$–$C_4$alkylsulfonamide, hydroxy, or carboxy;

$L_1$ is not $C_1$–$C_2$alkyl, except when $R_1$ is hydroxy-substituted 2-benzimidazole, $L_1$ includes $C_1$–$C_2$alkyl;

$L_1$ and $L_2$ are independently $C_1$–$C_4$alkyl, $C_1$–$C_4$alkenyl, $C_1$–$C_4$alkynyl, $C_1$–$C_4$alkoxy, amino$C_1$–$C_4$alkyl, hydroxy$C_1$–$C_4$alkyl, carbonyl, cyclo$C_3$–$C_6$alkyl or aminocarbonyl; and optionally substituted at any of the 2, 3, 5, or 6 positions independently with X, wherein X is hydroxy, amino, $C_1$–$C_4$alkylamino, di($C_1$–$C_4$)alkylamino, $C_1$–$C_4$alkyl, ester, carbamate, carbonate, or ether.

As used herein, "alkyl" as well as other groups having the prefix "alk" such as, for example, alkoxy, alkanoyl, alkenyl, alkynyl and the like, means carbon chains which may be linear or branched or combinations thereof. Examples of alkyl groups include methyl, ethyl, propyl, isopropyl, butyl, sec- and tert-butyl, pentyl, hexyl, heptyl and the like. "Alkenyl", "alkynyl" and other like terms include carbon chains containing at least one unsaturated C—C bond.

The term "cycloalkyl" means carbocycles containing no heteroatoms, and includes mono-, bi- and tricyclic saturated carbocycles, as well as fused ring systems. Such fused ring systems can include one ring that is partially or fully unsaturated such as a benzene ring to form fused ring systems such as benzofused carbocycles. Cycloalkyl includes such fused ring systems as spirofused ring systems. Examples of cycloalkyl include cyclopropyl, cyclobutyl, cyclopentyl, cyclohexyl, decahydronaphthalene, adamantane, indanyl, indenyl, fluorenyl, 1,2,3,4-tetrahydronaphalene and the like. Similarly, "cycloalkenyl" means carbocycles containing no heteroatoms and at least one non-aromatic C—C double bond, and include mono-, bi-.and tricyclic partially saturated carbocycles, as well as benzofused cycloalkenes. Examples of cycloalkenyl include cyclohexenyl, indenyl, and the like.

Unless otherwise stated, the terms "carbonyl" and "aminocarbonyl" include short $C_1$–$C_2$ termini. The terms include, for example, —$CH_2CONH$—, —$CH_2CO$—, —$C_2H_4CONHCH_2$—, and —$CH_2COC_2H_4$—.

Unless otherwise stated, the term "carbamate" is used to include —$OCOOC_1$–$C_4$alkyl, —$NHCOOC_1$–$C_4$alkyl, and —$OCONHC_1$–$C_4$alkyl.

The term "halogen" includes fluorine, chlorine, bromine and iodine atoms.

The term "SEM" is used to describe —$CH_2$—O—$CH_2CH_2$—$Si(CH_3)_3$.

The term "$C_0$" means that the carbon is not present. Thus, "$C_0$–$C_5$" means that there are from none to five carbons present—that is, five, four, three, two, one, or no carbons present.

The term "optionally substituted" is intended to include both substituted and unsubstituted. Thus, for example, optionally substituted aryl could represent a pentafluorophenyl or a phenyl ring.

Compounds described herein contain one or more asymmetric centers and may thus give rise to diastereomers and optical isomers. The present invention includes all such possible diastereomers as well as their racemic mixtures, their substantially pure resolved enantiomers, all possible geometric isomers, and pharmaceutically acceptable salts thereof. The above Formula I is shown without a definitive stereochemistry at certain positions. The present invention includes all stereoisomers of Formula I and pharmaceutically acceptable salts thereof. Further, mixtures of stereoisomers as well as isolated specific stereoisomers are also included. During the course of the synthetic procedures used to prepare such compounds, or in using racemization or epimerization procedures known to those skilled in the art, the products of such procedures can be a mixture of stereoisomers.

The term "pharmaceutically acceptable salts" refers to salts prepared from pharmaceutically acceptable non-toxic bases or acids. When the compound of the present invention is acidic, its corresponding salt can be conveniently prepared from pharmaceutically acceptable non-toxic bases, including inorganic bases and organic bases. Salts derived from such inorganic bases include aluminum, ammonium, calcium, copper (ic and ous), ferric, ferrous, lithium, magnesium, manganese (ic and ous), potassium, sodium, zinc and the like salts. Particularly preferred are the ammonium, calcium, magnesium, potassium and sodium salts. Salts derived from pharmaceutically acceptable organic non-toxic bases include salts of primary, secondary, and tertiary amines, as well as cyclic amines and substituted amines such as naturally occurring and synthesized substituted amines. Other pharmaceutically acceptable organic non-toxic bases from which salts can be formed include ion exchange resins such as, for example, arginine, betaine, caffeine, choline, N,N'-dibenzylethylenediamine, diethylamine, 2-diethylaminoethanol, 2-dimethylaminoethanol, ethanolamine, ethylenediamine, N-ethylmorpholine, N-ethylpiperidine, glucamine, glucosamine, histidine, hydrabamine, isopropylamine, lysine, methylglucamine, morpholine, piperazine, piperidine, polyamine resins, procaine, purines, theobromine, triethylamine, trimethylamine, tripropylamine, tromethamine and the like.

When the compound of the present invention is basic, its corresponding salt can be conveniently prepared from pharmaceutically acceptable non-toxic acids, including inorganic and organic acids. Such acids include, for example, acetic, benzenesulfonic, benzoic, camphorsulfonic, citric, ethanesulfonic, fumaric, gluconic, glutamic, hydrobromic, hydrochloric, isethionic, lactic, maleic, malic, mandelic, methanesulfonic, mucic, nitric, pamoic, pantothenic, phosphoric, succinic, sulfuric, tartaric, p-toluenesulfonic acid and the like. Particularly preferred are citric, hydrobromic, hydrochloric, maleic, phosphoric, sulfuric, and tartaric acids.

The pharmaceutical compositions of the present invention comprise a compound represented by Formula I (or pharmaceutically acceptable salts thereof) as an active ingredient, a pharmaceutically acceptable carrier and optionally other therapeutic ingredients or adjuvants. The compositions include compositions suitable for oral, rectal, topical, and parenteral (including subcutaneous, intramuscular, and intravenous) administration, although the most suitable route in any given case will depend on the particular host, and nature and severity of the conditions for which the active ingredient is being administered. The pharmaceutical compositions may be conveniently presented in unit dosage form and prepared by any of the methods well known in the art of pharmacy.

In practice, the compounds represented by Formula I, or pharmaceutically acceptable salts thereof, of this invention can be combined as the active ingredient in intimate admixture with a pharmaceutical carrier according to conventional pharmaceutical compounding techniques. The carrier may take a wide variety of forms depending on the form of preparation desired for administration, e.g., oral or parenteral (including intravenous). Thus, the pharmaceutical compositions of the present invention can be presented as discrete units suitable for oral administration such as capsules, cachets or tablets each containing a predetermined amount of the active ingredient. Further, the compositions can be presented as a powder, as granules, as a solution, as a suspension in an aqueous liquid, as a non-aqueous liquid, as an oil-in-water emulsion or as a water-in-oil liquid emulsion. In addition to the common dosage forms set out above, the compound represented-by Formula I, or pharmaceutically acceptable salts thereof, may also be administered by controlled release means and/or delivery devices. The compositions may be prepared by any of the methods of pharmacy. In general, such methods include a step of bringing into association the active ingredient with the carrier that constitutes one or more necessary ingredients. In general, the compositions are prepared by uniformly and intimately admixing the active ingredient with liquid carriers or finely divided solid carriers or both. The product can then be conveniently shaped into the desired presentation.

Thus, the pharmaceutical compositions of this invention may include a pharmaceutically acceptable carrier and a compound or a pharmaceutically acceptable salt of Formula I. The compounds of Formula I, or pharmaceutically acceptable salts thereof, can also be included in pharmaceutical compositions in combination with one or more other therapeutically active compounds.

The pharmaceutical carrier employed can be, for example, a solid, liquid, or gas. Examples of solid carriers include lactose, terra alba, sucrose, talc, gelatin, agar, pectin, acacia, magnesium stearate, and stearic acid. Examples of liquid carriers are sugar syrup, peanut oil, olive oil, and water. Examples of gaseous carriers include carbon dioxide and nitrogen.

In preparing the compositions for oral dosage form, any convenient pharmaceutical media may be employed. For example, water, glycols, oils, alcohols, flavoring agents, preservatives, coloring agents and the like may be used to form oral liquid preparations such as suspensions, elixirs and solutions; while carriers such as starches, sugars, microcrystalline cellulose, diluents, granulating agents, lubricants, binders, disintegrating agents, and the like may be used to form oral solid preparations such as powders, capsules and tablets. Because of their ease of administration, tablets and capsules are the preferred oral dosage units whereby solid pharmaceutical carriers are employed. Optionally, tablets may be coated by standard aqueous or nonaqueous techniques A tablet containing the composition of this invention may be prepared by compression or molding, optionally with one or more accessory ingredients or adjuvants. Compressed tablets may be prepared by compressing, in a suitable machine, the active ingredient in a free-flowing form such as powder or granules, optionally mixed with a binder, lubricant, inert diluent, surface active or dispersing agent. Molded tablets may be made by molding in a suitable machine, a mixture of the powdered compound moistened with an inert liquid diluent. Each tablet preferably contains from about 1 mg to about 500 mg of the active ingredient and each cachet or capsule preferably containing from about 1 to about 500 mg of the active ingredient.

Pharmaceutical compositions of the present invention suitable for parenteral administration may be prepared as solutions or suspensions of the active compounds in water. A suitable surfactant can be included such as, for example, hydroxypropylcellulose. Dispersions can also be prepared in glycerol, liquid polyethylene glycols, and mixtures thereof in oils. Further, a preservative can be included to prevent the detrimental growth of microorganisms.

Pharmaceutical compositions of the present invention suitable for injectable use include sterile aqueous solutions or dispersions. Furthermore, the compositions can be in the form of sterile powders for the extemporaneous preparation of such sterile injectable solutions or dispersions. In all cases, the final injectable form must be sterile and must be effectively fluid for easy syringability. The pharmaceutical compositions must be stable under the conditions of manufacture and storage; thus, preferably should be preserved against the contaminating action of microorganisms such as bacteria and fungi. The carrier can be a solvent or dispersion medium containing, for example, water, ethanol, polyol (e.g. glycerol, propylene glycol and liquid polyethylene glycol), vegetable oils, and suitable mixtures thereof.

Pharmaceutical compositions of the present invention can be in a form suitable for topical use such as, for example, an aerosol, cream, ointment, lotion, dusting powder, or the like. Further, the compositions can be in a form suitable for use in transdermal devices. These formulations may be prepared, utilizing a compound represented by Formula I of this invention, or pharmaceutically acceptable salts thereof, via conventional processing methods. As an example, a cream or ointment is prepared by mixing hydrophilic material and water, together with about 5 wt % to about 10 wt % of the compound, to produce a cream or ointment having a desired consistency.

Pharmaceutical compositions of this invention can be in a form suitable for rectal administration wherein the carrier is a solid. It is preferable that the mixture forms unit dose suppositories. Suitable carriers include cocoa butter and other materials commonly used in the art. The suppositories may be conveniently formed by first admixing the composition with the softened or melted carrier(s) followed by chilling and shaping in moulds.

In addition to the aforementioned carrier ingredients, the pharmaceutical formulations described above may include, as appropriate, one or more additional carrier ingredients such as diluents, buffers, flavoring agents, binders, surface-active agents, thickeners, lubricants, preservatives (including anti-oxidants) and the like. Furthermore, other adjuvants can be included to render the formulation isotonic with the blood of the intended recipient. Compositions containing a compound described by Formula I, or pharmaceutically acceptable salts thereof, may also be prepared in powder or liquid concentrate form.

Experimental Protocols
Assessing the Activity of Selected Compounds to Inhibit. NR1A/2B NMDA Receptor Activation (FLIPR Assay)

The activity of selected compounds to inhibit NR1A/2B NMDA receptor activation measured as NR1A/2B receptor-mediated $Ca^{2+}$ influx is assessed by the following procedure.

NR1A/2B receptor transfected L(tk) cells are plated in 96-well format at $3 \times 10^6$ cells per plate and grown for one—two days in normal growth media (Dulbeccos MEM with Na pyruvate, 4500 mgglucose, pen/strep, glutamine, 10% FCS and 0.5 mg/ml geneticin). NR1A/2B-expression in these cells is induced by the addition of 4 nM dexamethasone in the presence of 500 $\mu$M ketamine for 16–24 hours. After receptor induction cells are washed using a Labsystem Cellwasher two times with assay buffer (Hanks balanced salt solution (IBSS-$Mg^{++}$ free) containing 20 mM HEPES, 0.1% BSA, 2mM $CaCl_2$ and 250 $\mu$M probenecid). The cells of each 96 well cell plate are loaded with the $Ca^{++}$ sensitive dye Fluo-3 (Molecular Probes, Inc.) at 4 $\mu$M in assay buffer containing 0.5% FBS, and 0.04% pluronic F-127 (Molecular Probes, Inc.) for 1 h at 37° C. avoiding light. The cells are then washed with the Cellwasher four times with assay buffer leaving them in 100 $\mu$l buffer. Test compounds in solution are pipetted by FLIPR (Fluorometric Imaging Plate Reader) into each test well for a 2 min pretreatment. During this time the fluorescence intensity is recorded (excitation at 488 nm and emission at 530 nm). The glutamate/glycine 50 $\mu$l agonist solution (final concentration 1 $\mu$M/1 $\mu$M) is then added by FLIPR into, each well already containing 150 $\mu$l of buffer (containing the test compound or vehicle) and the fluorescence is continuously monitored for 10 min. The endpoint fluorescence values are used to determine an $IC_{50}$ value comparing the agonist-stimulated signal for the vehicle alone sample and that for the cells incubated with each concentration of test compound.

Determining the Apparent Dissociation Constant (Ki) of Compounds for Human NR1A/NR2B Receptors (Binding Assay):

The radioligand binding assay is performed at room temperature in 96-well microtiter plates with a final assay volume of 1.0 mL in 20 mM Hepes buffer (pH 7.4) containing 150 mM NaCl. Solutions of test compounds were prepared in DMSO and serially diluted with DMSO to yield 20 $\mu$L of each of 10 solutions differing by 3-fold in concentration. Non-specific binding (NSB) using hot AMD-1 (10 $\mu$M final concentration) and total binding (TB) by using DMSO (2% final concentration). A solution of NR1A/NR2B receptors (40 $\mu$M final concentration) and tritiated AMD-2 (1 nM final concentration) were added to the test compounds. After 3 h of incubation at room temperature, samples are filtered through Packard GF/B filters (presoaked in 0.05% PEI, polyethyleninine Sigma P-3143) and washed 10 times with 1 mL of cold 20 mM Hepes buffer per wash. After vacuum drying of the filter plates, 40 $\mu$L of Packard Microscint-20 was added and bound radioactivity determined in a Packard TopCount. The apparent dissociation constant (Ki), the maximum percentage inhibition ($\%I_{max}$), the minimum percentage inhibition ($\%I_{min}$) and the hill slope (nH) were determined by a non-linear least squares fitting the bound CPM data to Equation #1 below.

Equation #1:

$$CPM\ Bound = \frac{(SB)(\%\ I_{max} - \%\ I_{min})}{\left(1 + \{[Drug]/\{Ki[L\text{-}844, 345]/K_D\}\}^{nH}\right)} + NSB + (SB)(1 - \%\ I_{max})$$

where, $K_D$ is the apparent dissociation constant for the radioligand for the receptor as determined by hot saturation and SB is the specifically bound CPM determined from the difference of TB and NSB.

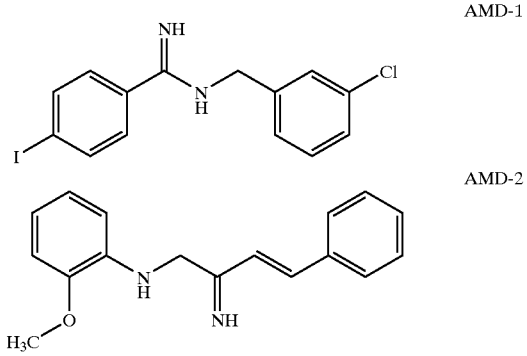

AMD-1

AMD-2

Compounds AMD-1 and AMD-2 can be synthesized in accordance with the following general reaction schemes.

SCHEME 1

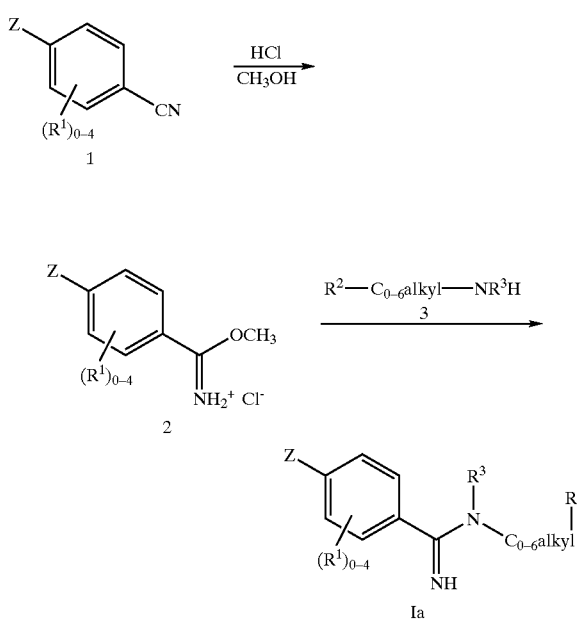

In accordance with scheme 1, hydrogen chloride is bubbled through a solution of the appropriately substituted benzonitrile 1 in methanol at room temperature. The volatiles are removed under reduced pressure and the resulting residue is triturated with ether and filtered to yield the desired imidate 2. Imidate 2 is dissolved in methanol at ambient temperature, treated with amine 3 at ambient temperature and stirred under argon. The volatiles are removed under reduced pressure and the residue purified by preparative HPLC or trituration with ether to afford amidine Ia.

SCHEME 2

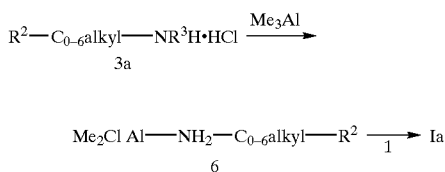

In accordance with scheme 2, at room temperature under argon, amine 3a is dissolved in ether and was treated with 1-M hydrogen chloride in ether (1 equiv.) in a single portion. The resulting precipitate is stirred vigorously for 10 minutes. The volatiles are removed under reduced pressure. The residue is suspended in toluene, cooled to 0° C. under argon, treated with 2.0-M trimethylaluminum (1.05 equiv.) in a dropwise manner, and stirred for 45 minutes at room temperature to afford intermediate 6 (not isolated). Compound 6 is added to a solution of nitrile 1 in toluene. The reaction is heated to 80° C. without stirring in a sealed tube for 18 h, cooled to ambient temperature, poured onto a silica gel column and eluted with methanol/dichloromethane to give the amidine 4.

Preparation of [$^{125}$I]AMD-1

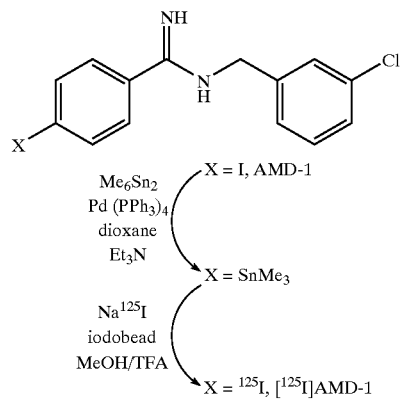

Tritiated AM-1 was prepared by the following procedure: A mixture of AMD-1, hydrochloride salt, (5 mg, 0.012 mmol) in dioxane (0.2 mL) containing triethylamine (4 μL) was treated with hexamethylditin (5 μL), a catalytic amount of palladium catalyst and heated at 100° C. for 45 minutes. The reaction was cooled to room temperature, filtered through a glass wool plug, rinsed with methanol and concentrated in vacuo to give 10.7 mg of a brown oil. The oil was dissolved in methylene chloride and passed through a small silica column eluting with methylene chloride followed by 5% methanol/methylene chloride. Fractions containing the trimethylstannane (Rf 0.26 in 10% methanol/methylene chloride) were pooled and concentrated in vacuo to give 4.5 mg of the trimethylstannane as a clear colorless oil. This material was further purified by HPLC ($C_{18}$ Econosil, 10×250 mm, 20 minute linear gradient, 30% MeCN:70% $H_2O$ (0.1% TFA) to 90% MeCN, 3 mL/min, 254 nm, retention time 15 minutes) to give 3 mg of the trimethylstannane.

A Na $^{125}$I shipping vial (10 mCi, Amersham) was charged with a stir bar, an iodobead, 50 μL of methanol and stirred five minutes at room temperature. A solution of the trimethylstannane (0.1 mg) in 50 μL of methanol containing 5 μL of trifluoroacetic acid was added and the reaction was stirred for five minutes. The reaction was quenched with 50 μL of ammonium hydroxide and purified by HPLC (C 18 Vydac protein and peptide column, 4.6×250 mm, 20 minute linear gradient, 30% MeCN:70% $H_2O$ (0.1% TFA) to 90% MeCN, 1 mL/min, retention time 11 minutes). Fractions containing the radioactive product were pooled and concentrated in vacuo to give 989 μCi of [$^{125}$I]AMD-1 with a specific activity of 898 Ci/mmol as measured by UV absorbance at 272 nm.

Synthesis of Tritiated AMD-2

Tritiated AMD-2 was prepared by the following procedure: The phenol of AMD-2 (2 mg, 0.008 mmol) dissolved in dimethylformamide (0.6 mL) and potasium carbonate (1.2 mg) for 1 hr. High specific activity tritiated methyl iodide (50 mCi, 0.0006 mmol, in toluene 1 mL, American Radiolabeled Chemicals) was added at room temperature and stirred for 2 hours. The reaction mixture was filtered using a Whatman PTFE 0.45 μm syringeless filter device to remove any insoluable potassium carbonate, washed with Abs. ethanol (2 mL, Pharmco), and the combined filtrates were concentrated to dryness at room temperature using a rotary evaporator; this also removed any unreacted tritiated methyl iodide. The residue was purified by HPLC chromatography on a Phenomenx Luna C8 semi-prep column (Luna 5 micro C8(2), 250×10.0 mm) using a gradient system of 20/80 acetonitrile/water with 0.1% trifluoroacetic acid to 100% acetronitrile with 0.1% trifluoroacetic acid in 20 min. Total activity of the product was 8 mCi. Further purification was effected by absorption onto a Waters C-18 Sep-pak column (Waters Sep-Pak PLUS C18) and elution with water followed by absolute ethanol. The product was diluted with absolute ethanol (10 mL) before submission for final analysis.

The compounds of this invention exhibit less than 50 $\mu$M in the FLIBR and binding assays. Thus, the compounds and pharmaceutical compositions of this invention have been found to exhibit biological activity as NMDA NR2B antagonists. Accordingly, another aspect of the invention is the treatment of pain, migraine, depression, anxiety, schizophrenia, Parkinson's disease, or stroke—maladies that are amenable to amelioration through inhibition of NMDA NR2B receptors—by the administration of an effective amount of the compounds of this invention.

The following examples are provided to more fully illustrate the present invention, and are not to be construed as limiting the scope of the claims in any manner.

EXAMPLES

The compounds of this invention can be prepared by procedures similar to Scheme 1 shown below but modified by the utilization of other reactants in place of 1-SEM-benzimidole-2-carboxaldehyde.

In Scheme 1 above, in place of the 1-SEM-benzimidole-2-carboxaldehyde

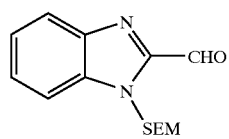

any of the following aldehydes or ketones can be used to prepare the compounds of this invention:

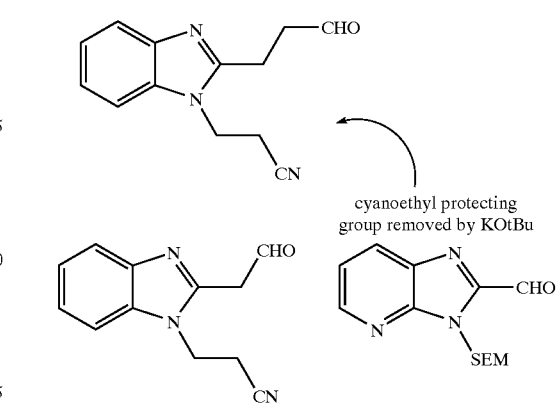

-continued

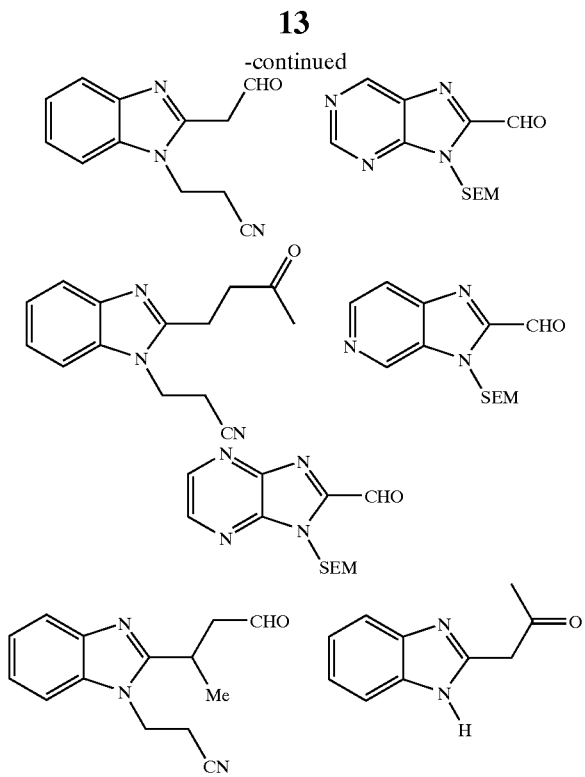

KNOWN EXAMPLE 2-(4-Benzyl-piperidin-1-ylmethyl)-1H-benzimidazole

Example 1 was prepared by the following procedure.

step 1:

1-(2-Trimethylsilylethoxymethyl)-1H-benzoimidazole:

A mixture of KH, from 7 g of 30% oil dispersion, and 5 g of benzimidazole in 100 mL of THF was stirred under nitrogen at room temperature for 18 h. To the stirred suspension was added 7 g of 2-trimethylsilylethoxymethyl chloride and the mixture kept at room temperature for 24 h, cooled in an ice bath, cautiously quenched with 50 mL of water, and extracted into ether. The combined ether extracts were dried over magnesium sulfate and concentrated. Low pressure chromatography over silica gel eluting with a gradient of 3:1 ethyl acetate:hexane to 100% ethyl acetate gave 9.5 g of 1-SEM-benzimidazole as a colorless oil.

Step 2:

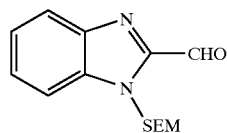

1-(2-Trimethylsilylethoxymethyl)-1H-benzoimidazole-2-carbaldehyde:

To a solution of 40 mmole of lithium diisopropylamide in 100 mL of THF cooled to −78° C. was added 5 g of 1-SEM-benzimidazole in 50 mL of THF. After 1.5 h at or below −70° C., the red solution was quenched by rapid addition of 6 mL of methyl formate. After warming to room temperature over 30 min, 50 mL of water and 200 mL of ethyl acetate were added. The organic layer was separated and dried over magnesium sulfate then concentrated under reduced pressure to 5.3 g of a thick oil that solidified in the freezer.

Step 3:

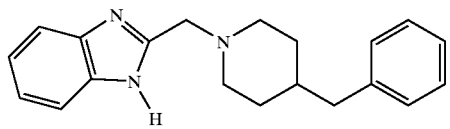

2-(4-Benzyl-piperidin-1-ylmethyl)-1H-benzimidazole:

A mixture of 0.5 g of 4-benzyl-piperidine, 0.5 g of 1-(2-trimethylsilylethoxymethyl)-1H-benzoimidazole-2-carbaldehyde, 5 mL of 1,2-dichloroethane and 0.5 g of sodium triacetoxyborohydride was stirred at room temperature for 48 h. The reaction mixture was diluted with 50 mL chloroform and 10 mL saturated aqueous Na₂CO₃ and the layers separated. The aqueous layer was extracted with 2×25 mL of chloroform and the combined organic layers dried over magnesium sulfate and concentrated under reduced pressure. The crude SEM ether was heated to reflux in 50 mL of ethanol containing 5 mL of 3N HCl for 2 h, cooled, concentrated and partitioned between 10 mL of saturated aqueous sodium carbonate and 3×25 mL of chloroform. The chloroform extracts were dried over magnesium sulfate and concentrated. Purification by chromatography eluting with 90:10 CHCl₃: MeOH gave 0.8 g of 2-[4-benzyl-piperidin-1-ylmethyl]-1H-benzimidazole: MS (m+1)=: $^1$H NMR (400MHz, CDCl₃).

Example 1

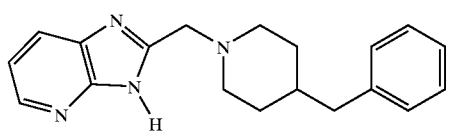

2-(4-Benzyl-piperidin-1-ylmethyl)-imidazo[4,5-b]pyridine

Example 1 was prepared in a similar manner to the Known Example above, but substituting 3H-imidazo[4,5-b]pyridine for benzimidazole in Step 1. Purification by chromatography eluting with 90:10 CHCl₃: MeOH gave 2-(4-benzyl-piperidin-1-ylmethyl)-imidazo[4,5-b]pyridine: MS (m+1)=307.4; $^1$H NMR (400 MHz, CDCl₃) 9.75 (br, 1H), 8.4 (d, 1H), 7.95 (d, 1H), 7.3–7.1 (m, 5H), 3.9 (s, 2H), 2.9 (d, 2H), 2.6 (d, 2H), 2.2 (dd, 2H), 1.7 (d, 2H), 1.7 (m, 1H), 1.4 (dd, 2H).

Example 2

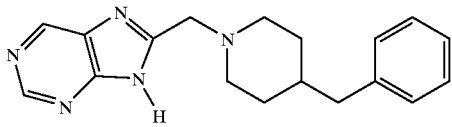

8-(4-Benzyl-piperidin-1-ylmethyl)-purine

Example 2 was prepared in a similar manner to the Known Example above, but substituting purine for benzimidazole in Step 1. Purification by chromatography eluting with 90:10:1 CHCl$_3$: MeOH:NH$_4$OH gave 8-(4-benzyl-piperidin-1-ylmethyl)-purine: MS (m+1)=308.4; $^1$H NMR (400 MHz, CDCl$_3$) 9.05 (s, 1H), 9.0 (s, 1H), 7.3–7.1 (m, 5H), 3.9 (s, 2H), 2.9 (d, 2H), 2.6 (d, 2H), 2.2 (dd, 2H), 1.7 (d, 2H), 1.7 (m, 1H), 1.4 (dd, 2H).

Example 3

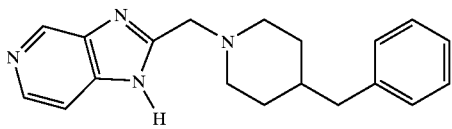

2-(4-Benzyl-piperidin-1-ylmethyl)-imidazo[4,5-c]pyridine

Example 3 was prepared in a similar manner to the Known Example above, but substituting 3H-imidazo[4,5-b]pyridine for benzimidazole in Step 1. Purification by chromatography eluting with 90:10:1 CHCl$_3$:MeOH:NH$_4$OH gave 2-(4-benzyl-piperidin-1-ylmethyl)-imidazo[4,5-c]pyridine: MS (m+1)=307.4; $^1$H NMR (400 MHz, CDCl$_3$) 9.75 (br, 1H), 8.4 (d, 1H), 7.95 (d, 1H), 7.3–7.1 (m, 6H), 3.90 (s, 2H), 2.90 (d, 2H), 2.6 (d, 2H), 2.2 (dd, 2H), 1.7 (d, 2H), 1:7 (m, 1H), 1.4 (dd, 2H).

Example 4

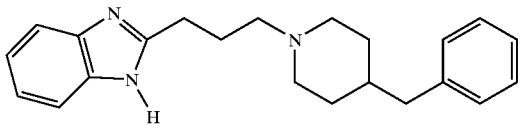

2-[3-(4-Benzyl-piperidin-1-yl)-propyl]-1H-benzimidazole

Example 4 was prepared by the following procedure.
Step 1:

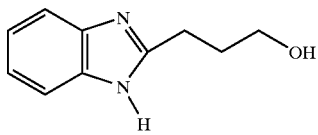

3-(1H-Benzimidazol-2-yl)-propan-1-ol:

A mixture of 5.4 g of 1,2-phenylenediamine and 4.5 g of dihydro-furan-2-one in 50 mL of 4N hydrochloric acid was heated to reflux for 20 h, 1 teaspoon of decolorizing carbon added, and after another 15 min reflux, filtered hot. The filtrate was concentrated under reduced pressure to near dryness, the residue made basic (pH=8) with saturated sodium bicarbonate and extracted into 3×80 mL of ether. The combined extracts were dried over magnesium sulfate and concentrated under reduced pressure. After drying under vacuum, 8.4 g of 3-(1H-benzimidazol-2-yl)-propan-1-ol was obtained as a solid.

Step 2:

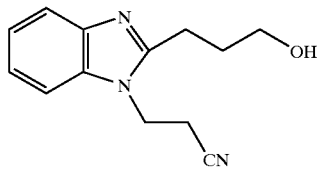

3-[2-(3-Hydroxy-propyl)-benzimidazol-1-yl]-propionitrile:

To a stirred solution of 3.8 g of 3-(1H-benzimidazol-2-yl)-propan-1-ol and 4 g dihydropyran in 500 mL of THF was added p-toluenesulfonic acid monohydrate until the pH was about 3 (indicator paper). After stirring overnight, an additional 2 mL of dihydropyran was added. After 2 additional hours, the conversion was complete. The mixture was concentrated under reduced pressure and partitioned between 250 mL of 1N NaOH and 2×250 mL of ether. After drying over magnesium sulfate the combined extracts were concentrated to dryness.

To a solution of the resulting crude oily 2-[3-(tetrahydro-pyran-2-yloxy)-propyl]-1H-benzimidazole (14 g) in 250 mL of acetonitrile was added 5 mL of acrylonitrile, 2 drops of 1M tetrabutylammonium fluoride in THF and 1 drop 10N NaOH. After heating to 85° C. for 16 h, conversion was complete (TLC elution with 90:10 methylene chloride:methanol). After concentration under reduced pressure, the residue was partitioned between 2×200 mL of ethyl acetate and 200 mL of water. The combined extracts were dried over magnesium sulfate and concentrated under reduced pressure.

The crude 3-{2-[3-(tetrahydro-pyran-2-yloxy)-propyl]-benzimidazol-1-yl}-propionitrile was stirred in 250 mL of methanol with sufficient p-toluenesulfonic acid monohydrate to make the solution acidic (pH=1–2). After stirring overnight, the solution was concentrated under reduced pressure, made basic (pH=8) with 1N sodium hydroxide and extracted into 8×50 mL of ethyl acetate. The aqueous layer was saturated with NaCl to aid in extraction of the product. The combined extracts were dried over magnesium sulfate and concentrated under reduced pressure. Chromatography using a gradient of ethyl acetate then 10% methanol in ethyl acetate followed by trituration with ether-hexane gave 4.8 g of 3-[2-(3-hydroxy-propyl)-benzimidazol-1-yl]-propionitrile as a solid.

Step 3:

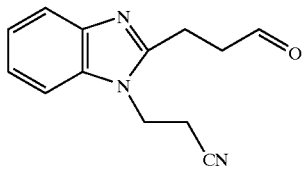

3-[2-(3-Oxo-propyl)-benimidazol-1-yl]-propionitrile:

To a stirred solution of 0.5 g of oxalyl chloride in 15 mL of methylene chloride cooled to −78° C. was added 1 mL of anhydrous DMSO. After 15 min, a solution of 1 g of 3-[2-(3-hydroxy-propyl)-benzimidazol-1-yl]-propionitrile in 50 mL of methylene chloride and 10 mL of anhydrous DMSO was added while keeping the temperature below −50° C. There was considerable precipitate which redissolved on warming to 0° C. over 20 min. After cooling back down to −50° C., 5 mL of triethyl amine was added and the mixture allowed to warm to room temperature. After 15 min, the mixture was diluted with 250 mL of water, shaken and separated. The organic layer was dried over magnesium sulfate and concentrated under reduced pressure. The crude 3-[2-(3-oxo-propyl)-benimidazol-1-yl]-propionitrile was an amber resin (1 g), and contained only traces of the starting alcohol by TLC (90:10 methylene chloride:methanol).
Step 4:

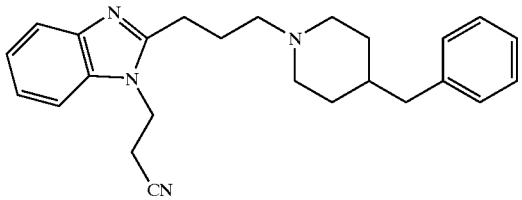

3-{2-[3-(3-Benzyl-8-aza-bicyclo[3.2.1]oct-8-yl)-propyl]-benzimidazol-1-yl}-propionitrile:

A mixture of 0.25 g of 4-benzyl-piperidine, 0.4 g of 1-3-[2-(3-oxo-propyl)-benimidazol-1-yl]-propionitrile, 5 mL of 1,2-dichloroethane and 0.3 g of sodium triacetoxyborohydride was stirred at room temperature for 24 h. The reaction mixture was diluted with 50 mL chloroform and 10 mL saturated aqueous Na$_2$CO$_3$ and the layers separated. The aqueous layer was extracted with 2×25 mL of chloroform and the combined organic layers dried over magnesium sulfate and concentrated under reduced pressure. Low pressure chromatography eluting with a gradient of 70:30 ethyl acetate:methanol to 70:30:5 ethyl acetate:methanol:triethylamine gave 400 mg of 3-{2-[3-(4-benzyl-piperidin-1-yl)-propyl]-benzoimidazol-1-yl}-propionitrile as a gum.
Step 5:

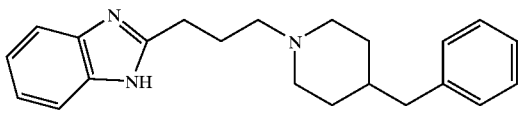

2-[3-(3-Benzyl-8-aza-bicyclo[3.2.1]oct-8-yl)-propyl]-1H-benzimidazole:

A mixture of 0.4 g of 3-{2-[3-(4-benzyl-piperidin-1-yl)-propyl]-benzoimidazol-1-yl}-propionitrile, 20 mL of isopropanol and 2 mL of 0.4 M sodium in isopropanol was heated to reflux for 2 h. Conversion was complete by TLC (80:20:1 ethyl acetate:methanol:triethylamine). The mixture was cooled, diluted with 10 mL of saturated sodium bicarbonate and concentrated. The residue was partitioned between 3×100 mL of chloroform and 50 mL of water. After drying over magnesium sulfate and concentration under reduced pressure, the residue was purified by preparative TLC eluting with 400:100:25 ethyl acetate:methanol:triethylamine. The major band (UV visualization) was 2-[3-(4-benzyl-piperidin-1-yl)-propyl]-1H-benzimidazole (220 mg): MS (m+1)=334.2; $^1$H NMR (400 MHz, CDCl$_3$) 7.4 (d, 2H), 7.32 (m, 2H), 7.25 (m, 1H), 7.2 (m, 4H), 3.1 (m, 4H), 2.65 (m, 2H), 2.6 (m, 2H), 2.1 (m, 2H), 2.0 (m, 2H), 1.8 (m, 2H), 1.7 (m, 1H), 1.5 (m, 2H).

Example 5

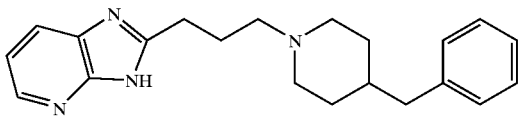

2-[3-(4-Benzyl-piperidin-1-yl)-propyl]-imidazo[4,5-b]pyridine

Example 5 was prepared by the following procedure.
Step 1:

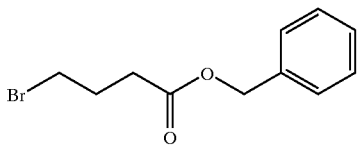

4-Bromo-butyric acid benzyl ester:

To an ice cold solution of 5 g of 4-bromobutyric acid and 5.5 g of benzylchloroformate in 100 mL of dichloromethane was added 5 mL of triethylamine and then 700 mg of 4-dimethylaminopyridine. A vigorous exothermic reaction ensued with evolution of carbon dioxide. After stirring for 3 h, the mixture was diluted with 100 mL of dichloromethane and washed with 200 mL of saturated sodium bicarbonate, dried over magnesium sulfate, and concentrated to an oil. Azeotropic drying with toluene gave 8 g of 4-bromobutyric acid benzyl ester as a clear oil.
Step 2:

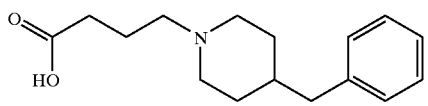

4-(4-Benzyl-piperidin-1-yl)-butyric acid:

A mixture of 0.9 g of 4-bromobutyric acid benzyl ester, 0.5 g of 4-benzylpiperidine, 0.6 mL of N,N-diisopropylethylamine and 20 mL of acetonitrile was heated to 80° C. for 4 h. The mixture was cooled, concentrated under reduced pressure and partitioned between chloroform and saturated sodium carbonate. After drying over magnesium sulfate the extracts were concentrated to a thick oil, 1.4 g, which was a mixture of the benzyl ester of 4-(4-benzyl-piperidin-1-yl)-butyric acid, benzyl 4- bromobutyrate and butyrolactone. Hydrogenation over 0.5 g of palladium on carbon in 100 mL of ethanol under 1 atm of hydrogen overnight gave 0.9 g of 4-(4-benzyl-piperidin-1-yl)-butyric acid after drying under vacuum at 100° C. overnight which was homogeneous by TLC (90:10:1 chloroform:methanol:ammonium hydroxide).
Step 4:

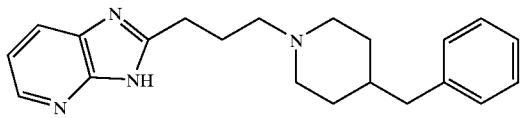

2-[3-(3-Benzyl-8-aza-bicyclo[3.2.1]oct-8-yl)-propyl]-3H-imidazo[4,5-b]pyridine:

A mixture of 0.6 g of 4-(4-benzyl-piperidin-1-yl)-butyric acid, 0.25 g of 1,2-diaminopyridine and 6 g of polyphosphoric acid was heated to 185° C. for 2 h. The mixture was cooled and stirred with 100 mL of 3N sodium hydroxide for 1 h after becoming homogeneous. The solution was extracted with 5×100 mL of chloroform and the combined extracts washed 3×50 mL of dilute ammonium hydroxide, heated with 1 g of decolorizing carbon for 10 min, cooled, filtered and concentrated. Purification of the residue by chromatography, eluting with 400:100:25 ethyl acetate:methanol:triethylamine gave 210 mg of 2-[3-(4-benzyl-piperidin-1-yl)-propyl]-imidazo[4,5-b]pyridine: MS (m+1)= 335.2; $^1$H NMR (400 MHz, CDCl$_3$) 8.36 (d, 1H), 7.8 (d, 1H), 7.6 (d, 0.5H), 7.3–7.1 (complex, 5.5H), 6.85 (d, 0.5H), 6.6 (dd 0.5H), 3.12 (dd, 2H), 3.0 (d, 2H), 2.6 (d, 2H), 2.55 (dd, 2H), 2.0 (m, 4H), 1.7 (d, 2H), 1.6 (m, 1H), 1.5 (m, 2H).

Example 6

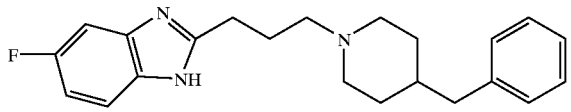

2-[3-(4-Benzyl-piperidin-1-yl)-propyl]-5-fluoro-1H-benzimidazole

Example 6 was prepared by the following procedure.

Step 1:

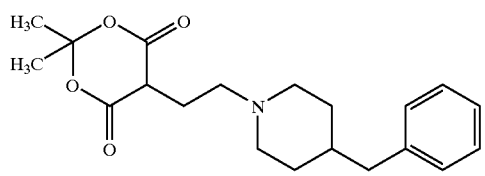

5-[2-(4-Benzyl-piperidin-1-yl)ethyl]-2,2-dimethyl-[1,3]dioxane-4,6-dione:

Following the procedure described in S. Danishefsky and R. K. Singh, *J. American Chemical Society*, 97:3239–3241 (1975), a mixture of 0.5 g of 4-benzylpiperidine, 10 mL of toluene, and 0.5 g, of 6,6-dimethyl-5,7-dioxaspiro[2.5] octane 4,8-dione was stirred for 20 h, cooled, and, the white solid product collected by filtration and dried under vacuum. The yield of 5-[2-(4-benzyl-piperidin-1-yl)-ethyl]-2,2-dimethyl-[1,3]dioxane-4,6-dione was 0.94 g.

Step 2:

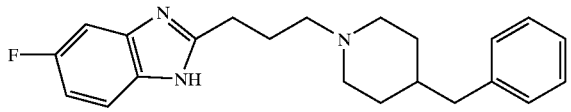

2-[3-(4-Benzyl-piperidin-1-yl)-propyl]-5-fluoro-1H-benzimidazole:

A mixture of 0.08 g of 5-[2-(4-benzyl-piperidin-1-yl)-ethyl]-2,2-dimethyl-[1,3]dioxane-4,6-dione, 10 mL of diglyme and 4 drops of conc hydrochloric acid was heated to reflux for 18 h. The mixture was cooled, and partitioned between dilute aqueous ammonium hydroxide and dichloromethane. The combined extracts were dried over magnesium sulfate and concentration under reduced pressure. The residue was purified by preparative TLC eluting with 70:30 chloroform:methanol. The major band (UV visualization) was 2-[3-(4-benzyl-piperidin-1-yl)-propyl]-5-fluoro-1H-benzimidazole (80 mg): MS (m+1)=352.4; $^1$H NMR (400 MHz, CDCl$_3$) 9.2 (br, 1H), 7.32 (m, 2H), 7.25 (m, 2H), 7.2 (m, 2H), 7.15 (m, 1H), 6.9 (dd, 1H), 3.1 (m, 4H), 2.65 (m, 2H), 2.6 (m, 2H), 2.1 (m, 2H), 2.0 (m, 2H), 1.8 (m, 2H), 1.7 (m, 1H), 1.5 (m, 2H).

Example 7

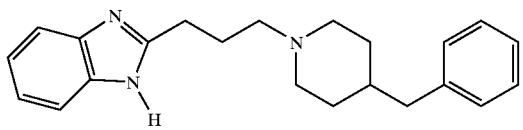

2-{3-[4-(4-Chloro-benzyl)-piperidin-1-yl]-propyl}-1H-benzimidazole

Example 7 was prepared by the following procedure.

Step 1:

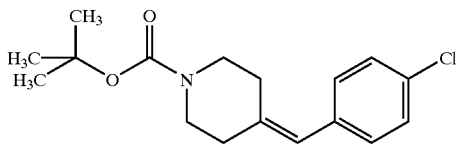

4-(4-Chloro-benzylidene)-piperidine-1-carboxylic acid tert-butyl ester:

To a stirred solution of 2 g of 4-oxo-piperidine-1-catboxylic acid tertbutyl ester and 3.5 g of diethyl 4-chlorobenzylphosphonate in 10 mL of 1,3-dimethyl-2-imidazolidinone dried over 4 Å mol sieves was added 0.50 g of 60% sodium hydride oil dispersion. The mixture was allowed to stir overnight, diluted with 200 mL of water and extracted with 3×100 mL of ether. Combined extracts were dried over magnesium sulfate and concentrated under reduced pressure. Low pressure chromatography over silica gel eluting with a gradient of 5:95 ethyl acetate:hexane to 1:5 ethyl acetate:hexane gave 2 g of 4-(4-chloro-benzylidene)-piperidine-1-carboxylic acid tert-butyl ester as a colorless oil.

Step 2:

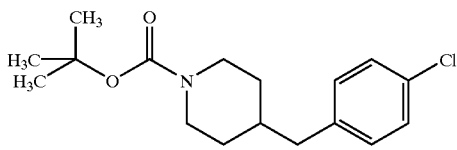

5-(4-Chloro-benzyl)-2-aza-bicyclo[2.2.2]octane-2-carboxylic acid ethyl ester:

A solution of 2 g of 4-(4-chloro-benzylidene)-piperidine-1-carboxylic acid tert-butyl ester and 0.5 g of 5% platinum on carbon in 10 mL of ethanol was allowed to stir overnight under 1 atm of hydrogen. The catalyst was filtered off and, the solution concentrated to give 2 g of 4-(4-chloro-benzyl)-piperidine-1-carboxylic acid tert-butyl ester as an oil.

Step 3:

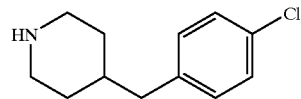

4-(4-Chloro-benzyl)-piperidine:

A mixture of 2 g of 4-(4-chloro-benzyl)-piperidine-1-carboxylic acid tert-butyl ester, dioxane (1.5 mL), and 3N hydrochloric acid (1.0 mL, 4equiv.) was heated at reflux for 3.5 hours. The cooled mixture was made basic with saturated sodium carbonate solution and extracted with chloroform (3×10 mL). The combined extracts were dried over magnesium sulfate and concentrated under reduced pressure. The crude product (1.2 g) was an oil.

Step 4 and 5:

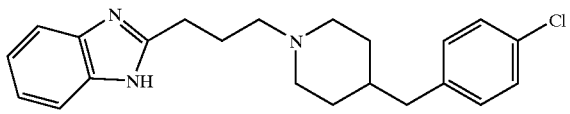

2-{3-[4-(4-Chloro-benzyl)-piperidin-1-yl]-propyl}-1H-benzimidazole:

Steps 4 and 5 were performed in a similar manner to Example 4, but substituting 4-(4-chloro-benzyl)-piperidine for 4-benzylpiperidine in Step 4. Purification by chromatography eluting with 90:10 CHCl$_3$: MeOH gave 2-{3-[4-(4-chloro-benzyl)-piperidin-1-yl]-propyl}-1H-benzimidazole: MS (m+1)=369; $^1$H NMR (400 MHz, CDCl$_3$) 9.75 (br, 1H), 7.7 (br, 1H), 7.5 (br, 1H), 7.4 (d, 2H), 7.32 (d, 2H), 7.2 (d, 2H), 3.1 (m, 4H), 2.65 (m, 2H), 2.6 (m, 2H), 2.1 (m, 2H), 2.0 (m, 2H), 1.75 (d, 2H), 1.7 (m, 1H), 1.5 (m, 2H).

Example 8

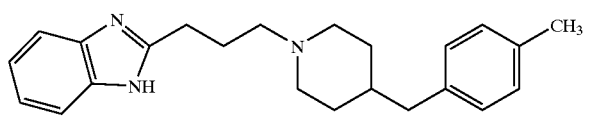

2-{3-[4-(4-Methyl-benzyl)-piperidin-1-yl]-propyl}-1H-benzimidazole

Example 8 was prepared in a similar manner to Example 6, but substituting 4-(4-methyl-benzyl)-piperidine for 4-(4-chloro-benzyl)-piperidine in Step 4. Purification by chromatography eluting with 90:10 CHCl$_3$:MeOH gave 2-{3-[4-(4-methyl-benzyl)-piperidin-1-yl]-propyl}-1H-benzimidazole: MS (m+1)=348.5; $^1$H NMR (400 MHz, CDCl$_3$) 9.75 (br, 1H), 7.7 (br, 1H), 7.5 (br, 1H), 7.4 (m, 2H), 7.3–7.2 dd, 4H), 3.1 (m, 4H), 2.65 (m, 2H), 2.6 (m,2H), 2.4 (s, 3H), 2.1 (m, 2H), 2.0 (m, 2H), 1.8 (d, 2H), 1.7 (m, 1H), 1.5 (m, 2H).

Example 9

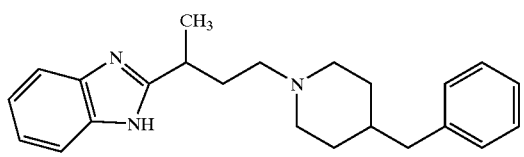

2-[3-(4-Benzyl-piperidin-1-yl)-1-methyl-propyl]-1H-benzimidazole

Example 9 was prepared by the following procedure.
Step 1:

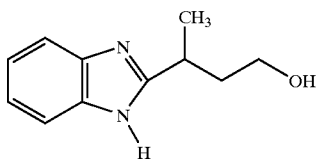

3-(1H-Benzimidazol-2-yl)-butan-1-ol:

Following the general procedure described in A. R. Friedman, D. S. Payne and A. R. Day, *J. Heterocyclic Chemistry*, 3:257–259(1966), a mixture of 9 g of 1,2-phenylenediamine dihydrochloride and 7 g of 2-methylbutyrolactone in 60 mL of 4N hydrochloric acid was heated to reflux for 4 days, 1 teaspoon of decolorizing carbon added, and after another 15 min reflux, filtered hot. The filtrate was concentrated under reduced pressure to near dryness, the residue made basic (pH=8) with ammonium hydroxide and extracted into 3×100 mL of ethyl acetate. The combined extracts were dried over magnesium sulfate and concentrated under reduced pressure. After drying under vacuum, 12 g of 3-(1H-benzimidazol-2-yl)-butan-1-ol was obtained as a resin.

Step 2:

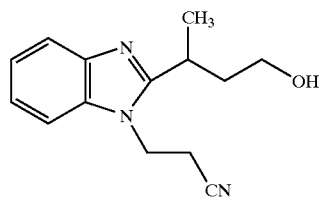

3-[2-(3-Hydroxy-1-methyl-propyl)-benzimidazol-1-yl]-propionitrile:

A mixture of 6 g of 3-(1H-benzimidazol-2-yl)-butan-1-ol, 20 mL of acetic acid and 5 mL of acetic anhydride was heated to reflux for 4 h. The mixture was cooled, concentrated, added 100 mL of methanol and again concentrated under reduced pressure. Azeotropically dried under reduced pressure with 200 mL of toluene, then under vacuum overnight. To a stirred solution of the crude acetate of 3-(1H-benzimidazol-2-yl)-butan-1-ol, 8.3 g, in 250 mL of acetonitrile was added 5 mL of acrylonitrile, 2 drops of 1M tetrabutylammonium fluoride in THF and dropwise 10N NaOH until basic. After heating to 85° C. for 16 h, the mixture was cooled, concentrated under reduced pressure, and partitioned between 2×300 mL of ethyl acetate and 100 mL of water. The combined extracts were dried over magnesium sulfate and concentrated under reduced pressure. The residue was triturated with 25 mL of ethyl acetate, cooled in an ice bath and filtered. The resulting white solid, 3.0 g, was 3-[2-(3-hydroxy-1-methyl-propyl)-benzimidazol-1-yl]-propionitrile.

Step 3:

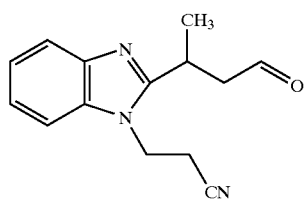

3-[2-(1-Methyl-3-oxo-propyl)-benzoimidazol-1-yl]-propionitrile:

To a stirred solution of 1.0 mL of oxalyl chloride in 20 mL of methylene chloride cooled to −78° C. was added 2 mL of anhydrous DMSO. After 15 min, a solution of 1 g of 3-[2-(3-hydroxy-1-methyl-propyl)-benzoimidazol-1-yl]-propionitrile in 20 mL of anhydrous DMSO and 50 mL of methylene chloride was added keeping the temperature below −50° C. After 10 min, 10 mL of triethyl amine was added and the mixture allowed to warm to room temperature. After 15 min, the mixture was diluted with 250 mL of water, shaken and separated. The organic layer was dried over magnesium sulfate and concentrated under reduced pressure. The crude 3-[2-(3-oxo-propyl)-benzimidazol-1-yl]-propionitrile was an amber resin (1.2 g), and contained only traces of the starting alcohol by TLC (90:10 methylene chloride:methanol).

Step 4:

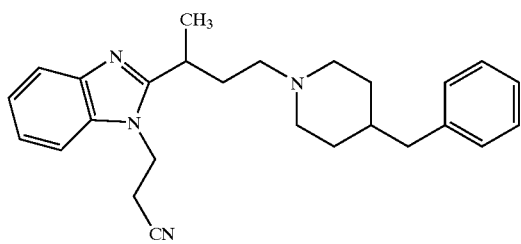

3-{2-[3-(4-Benzyl-piperidin-1-yl)-1-methyl-propyl]-benzimidazol-1-yl}-propionitrile:

A mixture of 0.3 g of 4-benzyl-piperidine, 0.2 g of 3-[2-(3-oxo-propyl)-benzimidazol-1-yl]-propionitrile, 5 mL of 1,2-dichloroethane and 0.3 g of sodium triacetoxyborohydride was stirred at room temperature for 24 h. The reaction mixture was diluted with 50 mL chloroform and 10 mL saturated aqueous $Na_2CO_3$ and the layers separated. The aqueous layer was extracted with 2×25 mL of chloroform and the combined organic layers dried over magnesium sulfate and concentrated under reduced pressure. Low pressure chromatography eluting with a gradient of 70:30 ethyl acetate:methanol to 80:20:2 ethyl acetate:methanol:triethylamine gave 205 mg of 3-{2-[3-(4-benzyl-piperidin-1-yl)-1-methyl-propyl]-benzimidazol-1-yl}-propionitrile as a gum.

Step 5:

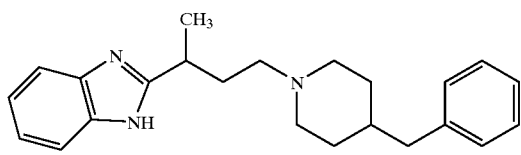

2-[3-(3-Benzyl-8-aza-bicyclo[3.2.1]oct-8-yl)-propyl]-1-H-benzimidazole:

A mixture of 0.2 g of 3-{2-[3-(4-benzyl-piperidin-1-yl)-1-methyl-propyl]-benzimidazol-1-yl}-propionitrile, 10 mL of tert-butanol and 1 g of potassium tert-butoxide was heated to reflux for 10 min. Conversion was complete by TLC (80:20:1 ethyl acetate:methanol:triethylamine). The mixture was cooled, diluted with 10 mL of saturated sodium bicarbonate and concentrated. The residue was partitioned between 3×100 mL of chloroform and 50 mL of water. After drying over magnesium sulfate and concentration under reduced pressure, the residue was purified by preparative TLC eluting with 450:50:10 chloroform:methanol:ammonium hydroxide.

The major band (UV visualization) was 2-[3-(4-benzyl-piperidin-1-yl)-1-methyl-propyl]-1H-benzimidazole (82 mg): MS (m+1)=348.5; $^1$H NMR (400 MHz, $CDCl_3$) 7.42 (s, 2H), 7.3 (m, 2H), 7.25 (m, 1H), 7.2 (m, 4H), 3.25 (m, 1H), 3.08 (m, 2H), 2.65 (d, 2H), 2.6 (m, 1H), 2.5 (m, 1H), 2.1 (m, 2H), 1.95 (m, 2H), 1.8 (d, 2H), 1.7 (m, 1H), 1.5 (d, 3H), 1.5 (m, 1H).

Example 10

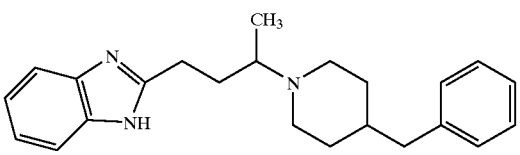

2-[3-(4-Benzyl-piperidin-1-yl)-butyl]-1H-benzimidazole

Example 10 was prepared by the following procedure.

Step 1:

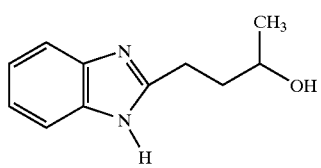

4-(1H-Benzimidazol-2-yl)-butan-2-ol:

A mixture of 8 g of 1,2-phenylenediamine and 6.6 g of 4-pentenoic acid in 50 mL of 4N hydrochloric acid was heated to reflux for 18 hours, cooled in an ice bath, made basic (pH=8) with ammonium hydroxide and extracted into 3×100 mL of ethyl acetate. The combined extracts were dried over magnesium sulfate and concentrated under reduced pressure. After drying under vacuum, 10 g of 4-(1H-benzimidazol-2-yl)-butan-2-ol was obtained as a thick oil which slowly crystallized.

Step 2:

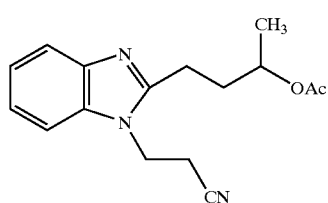

Acetic acid 3-[1-(2-cyano-ethyl)-1H-benzoimidazol-2-yl]-1-methyl-propyl ester:

A mixture of 6 g of 4-(1H-benzimidazol-2-yl)-butan-2-ol, 20 mL of acetic acid and 5 mL of acetic anhydride was heated to reflux for 6 h. The mixture was cooled, concentrated, added 100 mL of methanol and again concentrated under reduced pressure. Azeotropic drying under reduced pressure with 200 mL of toluene, then under vacuum overnight gave 8.3 g of the acetate of 4-(1H-benzimidazol-2-yl)-butan-2-ol as a crystalline solid. To a stirred solution of 7.5 g of the acetate of 4-(1H-benzimidazol-2-yl)-butan-2-ol in 250 mL of acetonitrile was added 5 mL of acrylonitrile, 2 drops of 1M tetrabutylammonium fluoride in THF and dropwise 10N NaOH until basic. After heating to 85° C. for 46 h, the mixture was cooled, concentrated under reduced pressure, and partitioned between 2×300 mL of ethyl acetate and 100 mL of water. The combined extracts were dried over magnesium sulfate and concentrated under reduced pressure. Purification of the residue by low pressure chromatography eluting with ethyl acetate gave 9.2 g of the acetate ester of 3-[2-(3-hydroxy-butyl)-benzimidazol-1-yl]-propionitrile as a resin.

Step 3:

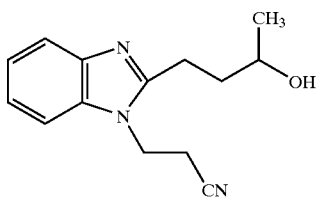

3-[2-(3-Hydroxy-butyl)-benzimidazol-1-yl]-propionitrile:

A mixture of 8.1 g of the acetate ester of 3-[2-(3-hydroxy-butyl)-benzimidazol-1-yl]-propionitrile (Product of Step 2), 100 mL of methanol, 25 mL of water and 1.2 g of lithium hydroxide monohydrate was stirred for 12 h at room temperature, concentrated under reduced pressure diluted with 50 mL of water and extracted with 3×100 mL portions of ethyl acetate. Combined extracts were dried over magnesium sulfate, concentrated under reduced pressure and dried azeotopically with toluene. Drying under vacuum gave 7.6 g of 3-[2-(3-hydroxy-butyl)-benzimidazol-1-yl]-propionitrile as a thick oil.

Step 4:

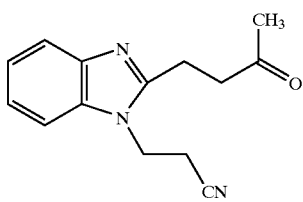

3-[2-(3-Oxo-butyl)-benzimidazol-1-yl]-propionitrile:

To a stirred solution of 1.0 mL of oxalyl chloride in 30 mL of methylene chloride cooled to −78° C. was added 2 mL of anhydrous DMSO. After 10 min, a solution of 2.1 g of 3-[2-(3-hydroxy-butyl)-benzimidazol-1-yl]-propionitrile in 150 mL of dichloromethane was added keeping the temperature below −50° C. After 10 min, 10 mL of triethyl amine was added and the mixture allowed to warm to room temperature. After 15 min, the mixture was diluted with 250 mL of water, shaken and separated. The organic layer was dried over magnesium sulfate and concentrated under reduced pressure. Drying under vacuum gave 2.2 g of 3-[2-(3-oxo-butyl)-benzimidazol-1-yl]-propionitrile as an amber resin.

Step 5:

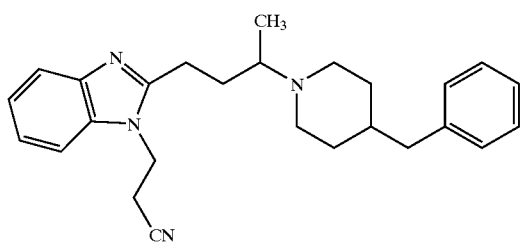

3-{2-[3-(4-Benzyl-piperidin-1-yl)-butyl]-benzimidazol-1-yl}-propionitrile:

A mixture of 0.3 g of 4-benzyl-piperidine, 0.24 g of 3-[2-(3-oxo-butyl)-benzimidazol-1-yl]-propionitrile, 5 mL of 1,2-dichloroethane and 0.3 g of sodium triacetoxyborohydride was stirred at room temperature for 3 days. The reaction mixture was diluted with 50 mL chloroform and 10 mL saturated aqueous $Na_2CO_3$ and the layers separated. The aqueous layer was extracted with 2×25 mL of chloroform and the combined organic layers dried over magnesium sulfate and concentrated under reduced pressure. Low pressure chromatography eluting with a gradient of 80:20 ethyl acetate:methanol to 80:20:5 ethyl acetate:methanol:triethylamine gave 320 mg of 3-{2-[3-(4-benzyl-piperidin-1-yl)-butyl]-benzimidazol-1-yl}-propionitrile as a resin.

Step 6:

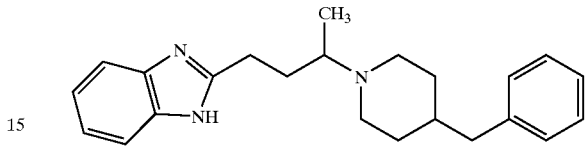

2-[3-(4-Benzyl-piperidin-1-yl)-butyl]-1H-benzimidazole:

A mixture of 0.32 g of 3-{2-[3-(4-benzyl-piperidin-1-yl)-butyl]-benzimidazol-1-yl}-propionitrile, 100 mL of tert-butanol and 1 g of potassium tert-butoxide was heated to reflux for 10 min. Conversion was complete by TLC (80:20:1 ethyl acetate:methanol:triethylamine). The mixture was cooled, diluted with 10 mL of saturated sodium bicarbonate and concentrated. The residue was partitioned between 3×100 mL of chloroform and 50 mL of water. After drying over magnesium sulfate and concentration under reduced pressure, the residue was purified by preparative TLC eluting with 90:10:2 chloroform:methanol:ammonium hydroxide. The major band (UV visualization) was 2-[3-(4-benzyl-piperidin-1-yl)-butyl]-1H-benzimidazole (250 mg): MS (m+1)=348.5; $^1$H NMR (400 MHz, $CDCl_3$) 7.42 (s, 2H), 7.3 (m, 2H), 7.25 (m, 1H), 7.2 (m, 4H), 3.25 (m, 1H), 3.0 (m, 2H), 2.8 (d, 2H), 2.65 (m, 2H), 2.5 (m, 2H), 2.1 (m, 2H), 1.6 (d, 2H), 1.3 (m, 1H), 1.2 (d, 3H), 1.0 (m, 1H).

Example 11

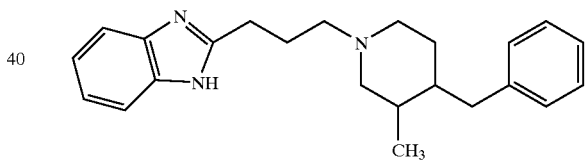

2-[3-(4-Benzyl-3-methyl-piperidin-1-yl)-propyl]-1H-benzimidazole

Example 11 was prepared by the following procedure.

Step 1:

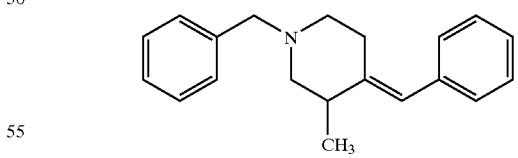

1-Benzyl-4-benzylidene-3-methyl-piperidine:

To a stirred solution of 2.1 g of 1-benzyl-3-methyl-piperidin-4-one and 2.5 g of diethyl benzylphosphonate in 5 mL of 1,3-dimethyl-2-imidazolidinone dried over 4 Å mol sieves was added 0.50 g of 60% sodium hydride oil dispersion. The mixture was allowed to stir 2 days, diluted with 400 mL of water and extracted with 3×50 mL of ether. Combined extracts were dried over magnesium sulfate and concentrated under reduced pressure. Low pressure chromatography over silica gel eluting with a gradient of 5:95 ethyl acetate:hexane to 1:4 ethyl acetate:hexane gave 2.7 g of 1-benzyl-4-benzylidene-3-methyl-piperidine as a colorless oil.

Step 2:

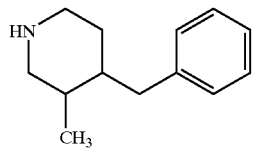

4-Benzyl-3-methyl-piperidine:

A solution of 2.7 g of 1-benzyl-4-benzylidene-3-methyl-piperidine and 2 g of 20% palladium hydroxide on carbon in 125 mL of ethanol was shaken 3 days under 55 psi of hydrogen. The catalyst was filtered off and the solution concentrated to give 2 g of a mixture of cis and trans-4-benzyl-3-methyl-piperidine as an oil.

Step 4 and 5:

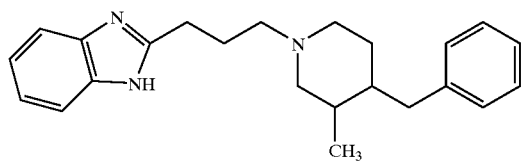

2-[3-(4-Benzyl-3-methyl-piperidin-1-yl)-propyl]-1H-benzimidazole:

Steps 4 and 5 were performed in a similar manner to Example 5, but substituting 4-benzyl-3-methyl-piperidine for 4-benzylpiperidine in Step 4. Purification by chromatography eluting with 225:20:5 chloroform:methanol:ammonium hydroxide gave cis and trans 2-[3-(4-benzyl-3-methyl-piperidin-1-yl)-propyl]-1H-benzimidazole as close moving bands: MS (m+1)=348.5; $^1$H NMR (400 MHz, CDCl$_3$) 7.58 (d, 2H), 7.2–7.0 (m, 7H), 3.0 (m, 4H), 2.5 (m, 4H), 2.0 (m, 2H), 1.6 (m, 2H), 1.1 (2×d, 3H), 1.0 (m, 2H).

Example 12

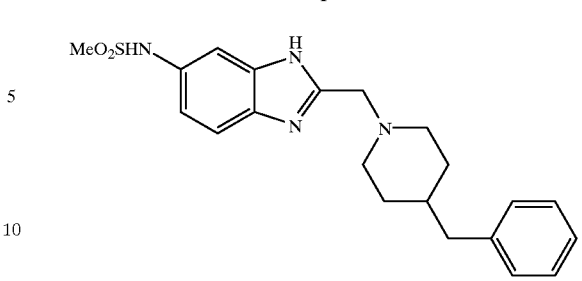

N-[2-(4-Benzyl-piperidin-1-ylmethyl)-3H-benzoimidazol-5-yl]-methanesulfonamide.

Example 12 was prepared by the following general procedure.

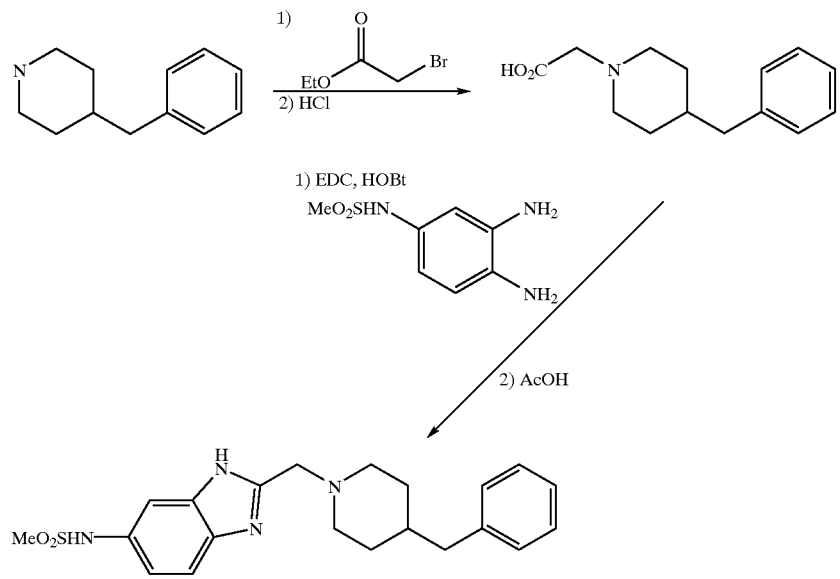

To a solution of 4-benzylpiperidine (1.0 g, 5.7 mmol) in DMF (20 mL) was added ethylbromoacetate (637 μL, 5.7 mmol) and the reaction mixture was stirred at room temperature for 4 h. The reaction mixture was partitioned between EtOAc and aqueous NaHCO$_3$, the organic layer was dried over Na$_2$SO$_4$, filtered and concentrated. The crude oil was purified by silica gel chromatography (gradient elution, 4:1 hexanes:EtOAc to EtOAc) to give the ethyl ester.

The ethyl ester (700 mg, 2.6 mmol) was dissolved in 6N HCl (5 mL) and heated to reflux for 1 h. The reaction mixture was cooled and concentrated to give

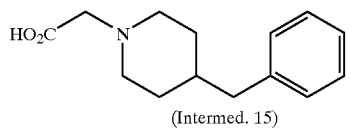

(Intermed. 15)

Intermed. 15 as a white solid.

To a solution of carboxylic acid Intermed. 15 (117 mg, 0.5 mmol) in DMF (3 mL) was added EDC (96 mg, 0.5 mmol), HOBt (68 mg, 0.5 mmol), and N-(3,4-diamino-phenyl)-methanesulfonamide (100 mg, 0.5 mmol). The reaction mixture was stirred at room temperature for 1 h followed by quenching with aqueous NaHCO₃ and EtOAc. The layers were separated and the organic was washed twice with water, dried over Na₂SO₄, filtered and concentrated. The crude oil was dissolved in AcOH and heated to reflux for 15 min. The reaction mixture was cooled, concentrated and purified by reverse-phase HPLC to give N-[2-(4-Benzyl-piperidin-1-ylmethyl)-3H-benzoimidazol-5-yl]-methanesulfonamide (90 mg): $^1$H NMR (300 MHz, CD₃OD) δ 7.82 (d, 1H), 7.77 (s, 1H), 7.49 (d, 1H), 7.32–7.17 (m, 5H), 4.92 (s, 2H), 3.70 (d, 2H), 3.02 (s, 2H), 2.60 (d, 2H), 2.00–1.88 (m, 3H), 1.70 (m, 2H); mass spectrum m/z 399 [(M+H)$^+$; calcd for $C_{21}H_{27}N_4O_2S$: 399].

What is claimed is:

1. A compound having the formula:

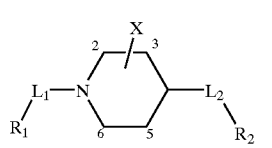

(I)

or a pharmaceutically acceptable salt thereof, wherein $R_1$ is 2-benzimidazole, 2-imidazopyridine, purine, or 2-quinazoline, each optionally substituted with one to five substituents, each substituent independently being chloro, fluoro, bromo, $C_1$–$C_4$alkyl, trifluoromethyl, $C_1$–$C_4$alkylsulfonamide, hydroxy, or carboxy;

$R_2$ is phenyl, optionally substituted with one to five substituents, each substituent independently being chloro, fluoro, bromo, $C_1$–$C_4$alkyl, trifluoromethyl, $C_1$–$C_4$alkylsulfonamide, hydroxy, or carboxy;

when $R_1$ is 2-benzimidazole, $L_1$ or $L_2$ is not $C_1$–$C_2$alkyl, except when $R_1$ is hydroxy-substituted 2-benzimidazole, $L_1$ or $L_2$ includes $C_1$–$C_2$alkyl;

$L_1$ and $L_2$ are independently $C_1$–$C_4$alkyl, $C_1$–$C_4$alkenyl, $C_1$–$C_4$alkynyl, $C_1$–$C_4$alkoxy, amino$C_1$–$C_4$alkyl, hydroxy$C_1$–$C_4$alkyl, carbonyl, cyclo$C_3$–$C_6$alkyl or aminocarbonyl; and optionally substituted at any of the 2, 3, 5, or 6 positions independently with X, wherein X is hydroxy, amino, $C_1$–$C_4$alkylamino, di($C_1$–$C_4$)alkylamino, $C_1$–$C_4$alkyl, $C_1$–$C_4$alkylester, —OCOO$C_1$–$C_4$alkyl, —NHCOO$C_1$–$C_4$alkyl, —OCONH$C_1$–$C_4$alkyl, $C_1$–$C_4$alkylcarbonate, or $C_1$–$C_4$alkylether.

2. The compound according to claim 1 or a pharmaceutically acceptable salt thereof, wherein $R_1$ is 2-imidazopyridine, optionally substituted with one to five substituents, each substituent independently being chloro, fluoro, bromo, ($C_1$–$C_4$alkyl, trifluoromethyl, $C_1$–$C_4$alkylsulfonamide, hydroxy, or carboxy;

$R_2$ is phenyl, optionally substituted with one to five substituents, each substituent independently being chloro, fluoro, bromo, $C_1$–$C_4$alkyl, trifluoromethyl, $C_1$–$C_4$alkylsulfonamide, hydroxy, or carboxy;

$L_1$ and $L_2$ are independently $C_1$–$C_4$alkyl, $C_1$–$C_4$alkenyl, $C_1$–$C_4$alkynyl, $C_1$–$C_4$alkoxy, amino$C_1$–$C_4$alkyl, hydroxy$C_1$–$C_4$alkyl, carbonyl, cyclo$C_3$–$C_6$alkyl or aminocarbonyl; and optionally substituted at any of the 2, 3, 5, or 6 positions independently with X, wherein X is hydroxy, amino, $C_1$–$C_4$alkylamino, di($C_1$–$C_4$)alkylamino, $C_1$–$C_4$alkyl, $C_1$–$C_4$alkylester, —OCOO$C_1$–$C_4$alkyl, —NHCOO$C_1$–$C_4$alkyl, —OCONH$C_1$–$C_4$alkyl, $C_1$–$C_4$alkylcarbonate, or $C_1$–$C_4$alkylether.

3. The compound according to claim 1 or a pharmaceutically acceptable salt thereof, wherein $R_1$ is purine, optionally substituted with one to five substituents, each substituent independently being chloro, fluoro, bromo, $C_1$–$C_4$alkyl, trifluoromethyl, $C_1$–$C_4$alkylsulfonamide, hydroxy, or carboxy;

$R_2$ is phenyl, optionally substituted with one to five substituents, each substituent independently being chloro, fluoro, bromo, $C_1$–$C_4$alkyl, trifluoromethyl, $C_1$–$C_4$alkylsulfonamide, hydroxy, or carboxy;

$L_1$ and $L_2$ are independently $C_1$–$C_4$alkyl, $C_1$–$C_4$alkenyl, $C_1$–$C_4$alkynyl, $C_1$–$C_4$alkoxy, amino$C_1$–$C_4$alkyl, hydroxy$C_1$–$C_4$alkyl, carbonyl, cyclo$C_3$–$C_6$alkyl or aminocarbonyl; and optionally substituted at any of the 2, 3, 5, or 6 positions independently with X, wherein X is hydroxy, amino, $C_1$–$C_4$alkylamino; di($C_1$–$C_4$)alkylamino, $C_1$–$C_4$alkyl, $C_1$–$C_4$alkylester, —OCOO$C_1$–$C_4$alkyl, —NHCOO$C_1$–$C_4$alkyl, —OCONH$C_1$–$C_4$alkyl, $C_1$–$C_4$alkylcarbonate, or $C_1$–$C_4$alkylether.

4. The compound according to claim 1 or a pharmaceutically acceptable salt thereof, wherein $R_1$ is 2-benzimidazole, optionally substituted with one to five substituents, each substituent independently being chloro, fluoro, bromo, $C_1$–$C_4$alkyl, trifluoromethyl, $C_1$–$C_4$alkylsulfonamide, hydroxy, or carboxy;

$R_2$ is phenyl, optionally substituted with one to five substituents, each substituent independently being chloro, fluoro, bromo, $C_1$–$C_4$alkyl, trifluoromethyl, $C_1$–$C_4$alkylsulfonamide, hydroxy, or carboxy;

$L_1$ is not $C_1$–$C_2$alkyl, except when $R_1$ is hydroxy-substituted 2-benzimidazole, $L_1$ includes $C_1$–$C_2$alkyl;

$L_1$ and $L_2$ are independently $C_1$–$C_4$alkyl, $C_1$–$C_4$alkenyl, $C_1$–$C_4$alkynyl, $C_1$–$C_4$alkoxy, amino$C_1$–$C_4$alkyl, hydroxy$C_1$–$C_4$alkyl, carbonyl, cyclo$C_3$–$C_6$alkyl or aminocarbonyl; and optionally substituted at any of the 2, 3, 5, or 6 positions independently with X, wherein X is hydroxy, amino, $C_1$–$C_4$alkylamino, di($C_1$–$C_4$)alkylamino, $C_1$–$C_4$alkyl, $C_1$–$C_4$alkylester, —OCOO$C_1$–$C_4$alkyl, —NHCOO$C_1$–$C_4$alkyl, —OCONH$C_1$–$C_4$alkyl, $C_1$–$C_4$alkylcarbonate, or $C_1$–$C_4$alkylether.

5. The compound according to claim 1, wherein said compound is 2-(4-Benzyl-piperidin-1-ylmethyl)-imidazo[4,5-b]pyridine;

8-(4-Benzyl-piperidin-1-ylmethyl)-pyrine;

2-(4-Benzyl-piperidin-1-ylmethyl)-imidazo[4,5-c]pyridine;

2-[3-(4-Benzyl-piperidin-1-yl)-propyl]-1H-benzimidazole;

2-[3-(4-Benzyl-piperidin-1-yl)-propyl]-imidazo[4,5-b]pyridine;

2-[3-(4-Benzyl-piperidin-1-yl)-propyl]-5-fluoro-1H-benzimidazole;

2-{3-[4-(4-Chloro-benzyl)-piperidin-1-yl]-propyl}-1H-benzimidazole;

2-{3-[4-(4-Methyl-benzyl)-piperidin-1-yl]-propyl}-1H-benzimidazole;

2-[3-(4-Benzyl-piperidin-1-yl)-1-methyl-propyl]-1H-benzimidazole;

2-[3-(4-Benzyl-piperidin-1-yl)-butyl]-1H-benzimidazole;

2-[3-(4-Benzyl-3-methyl-piperidin-1-yl)-propyl]-1H-benzimidazole; or

N-[2-(4-Benzyl-piperidin-1-ylmethyl)-3H-benzoimidazol-5-yl]-methanesulfonamide.

6. The compound according to claim 1, wherein said compound is

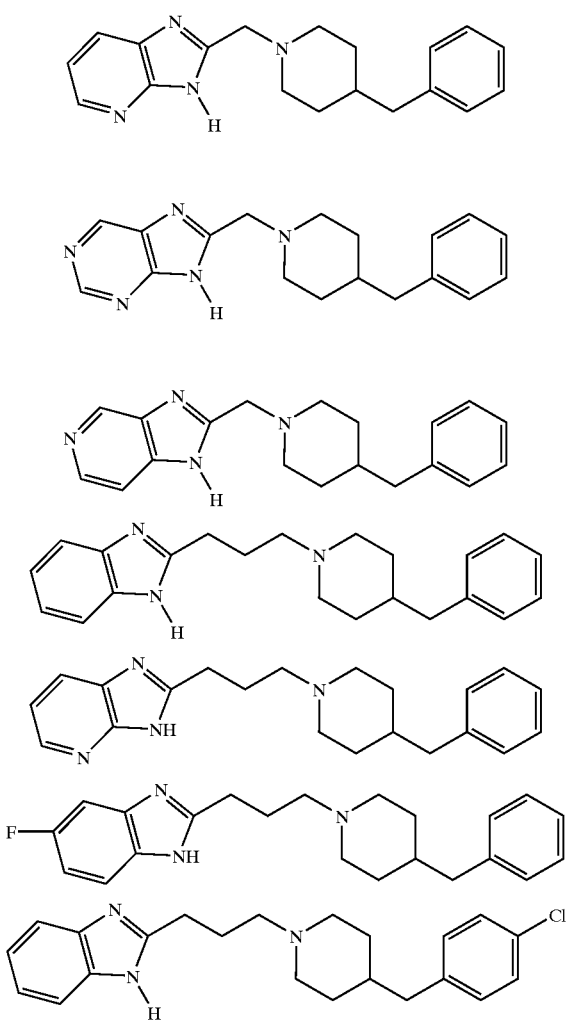

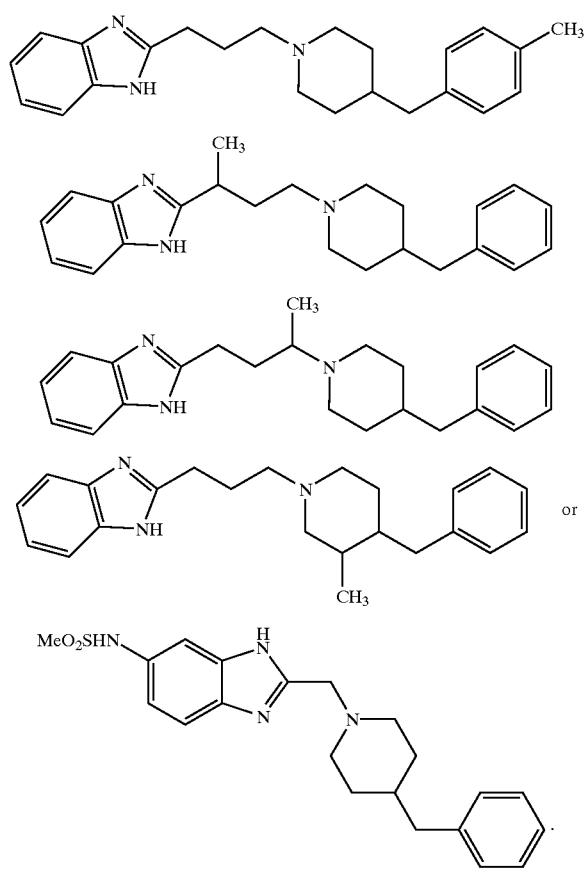

7. A pharmaceutical composition comprising an inert carrier and an effective amount of a compound according to claim 1.

8. A method of treating pain comprising a step of administering to one in need of such treatment an effective amount of a compound according to claim 1.

9. A method of treating migraine, depression, anxiety, schizophrenia, Parkinson's disease, or stroke comprising a step of administering to one in need of such treatment an effective amount of a compound according to claim 1.

* * * * *

UNITED STATES PATENT AND TRADEMARK OFFICE
CERTIFICATE OF CORRECTION

PATENT NO.    : 6,476,041 B1
DATED         : November 5, 2002
INVENTOR(S)   : Wayne Thompson et al.

It is certified that error appears in the above-identified patent and that said Letters Patent is hereby corrected as shown below:

<u>Column 29,</u>
Lines 27 through 31, should read:

-- $R_1$ is 2-benzimidazole, 2-imidazopyridine, or purine, each optionally substituted with one to five substitutents, each substituent independently being chloro, fluoro, bromo, $C_1$-$C_4$alkyl, trifluoromethyl, $C_1$-$C_4$alkylsulfonamide, hydroxy, or carboxy; --

Line 43, should read:
-- aminocarbonyl; wherein $R_1$ is attached to $L_1$ at a carbon atom of $R_1$; and --.

Signed and Sealed this

Eighth Day of July, 2003

JAMES E. ROGAN
*Director of the United States Patent and Trademark Office*

UNITED STATES PATENT AND TRADEMARK OFFICE
CERTIFICATE OF CORRECTION

PATENT NO. : 6,476,041 B1 Page 1 of 1
DATED : November 5, 2002
INVENTOR(S) : Wayne Thompson et al.

It is certified that error appears in the above-identified patent and that said Letters Patent is hereby corrected as shown below:

<u>Title page,</u>
Item [73], Assignee, should read -- Merck & Co., Inc., Rahway, NJ (US) and Merck Sharp & Dohme Ltd., Hoddesdon, Hertfordshire, England (UK) --

Signed and Sealed this

Fourth Day of November, 2003

JAMES E. ROGAN
*Director of the United States Patent and Trademark Office*